United States Patent [19]

Esin et al.

[11] Patent Number: 5,437,178
[45] Date of Patent: Aug. 1, 1995

[54] CONTROLLER FOR ULTRASONIC SENSORS

[75] Inventors: Alex Esin, Skokie; Lawrence J. Jones, Algonquin; Boris Rosselson, Des Plaines; Martin N. Sorenson, Buffalo Grove, all of Ill.

[73] Assignee: Kay-Ray/Sensall, Inc., Mount Prospect, Ill.

[21] Appl. No.: 909,538

[22] Filed: Jul. 6, 1992

[51] Int. Cl.⁶ ...................... G01N 29/24; A61B 10/00
[52] U.S. Cl. ...................... 73/1 DV; 73/612; 73/610; 73/628; 73/290 V; 367/7
[58] Field of Search ............ 73/1 DV, 610, 612, 626, 73/628, 641, 290 V, 32 AQ, 24.05, 592; 367/7

[56] References Cited

U.S. PATENT DOCUMENTS

| | | | |
|---|---|---|---|
| 3,964,297 | 6/1976 | Jorgensen et al. | 73/610 |
| 4,050,292 | 9/1977 | Bloch | 73/610 |
| 4,299,114 | 11/1981 | Silvermetz et al. | 73/1 H |
| 4,316,183 | 2/1982 | Palmer et al. | 340/621 |
| 4,384,491 | 5/1982 | Brown et al. | 73/861.28 |
| 4,448,207 | 5/1984 | Parrish | 128/771 |
| 4,470,299 | 9/1984 | Soltz | 73/290 V |
| 4,542,656 | 9/1985 | Johnson | 73/861.28 |
| 4,578,997 | 4/1986 | Soltz | 73/290 V |
| 4,655,084 | 4/1987 | Renzel | 73/612 |
| 4,676,098 | 6/1987 | Erlenkämper et al. | 73/290 V |
| 4,708,022 | 11/1987 | Johnson | 73/861.28 |
| 4,708,191 | 11/1987 | Block et al. | 164/150 |
| 4,715,226 | 12/1987 | Dorr | 73/290 V |
| 4,735,097 | 4/1988 | Lynnworth | 73/861.28 |
| 4,765,186 | 8/1988 | Dieulesaint et al. | 73/290 V |
| 4,770,038 | 9/1988 | Zuckerwar et al. | 73/290 V |
| 4,785,664 | 11/1988 | Reebe | 73/290 V |
| 4,787,407 | 11/1988 | Vogel | 137/2 |
| 4,815,323 | 3/1989 | Ellinger et al. | 73/290 |
| 4,821,569 | 4/1989 | Soltz | 73/290 V |
| 4,823,600 | 4/1989 | Biegel et al. | 73/592 |
| 4,833,918 | 5/1989 | Jean et al. | 73/290 V |
| 4,868,797 | 9/1989 | Soltz | 367/98 |
| 4,896,535 | 1/1990 | Duckart et al. | 73/290 V |
| 4,920,796 | 5/1990 | Duckart et al. | 73/290 V |
| 4,954,997 | 9/1990 | Dieulessaint et al. | 367/13 |
| 4,984,449 | 1/1991 | Caldwell et al. | 73/49.2 |
| 5,068,850 | 11/1991 | Moore | 370/85.8 |
| 5,140,558 | 8/1992 | Harrison, Jr. et al. | 367/7 |
| 5,205,175 | 4/1993 | Garza et al. | 73/628 |

Primary Examiner—Hezron E. Williams
Assistant Examiner—Rose M. Finley
Attorney, Agent, or Firm—Westman, Champlin & Kelly

[57] ABSTRACT

An ultrasonic transducer for measuring a property of a material within a defined space has a function of a velocity at which ultrasonic signals travel through the defined space includes a controller. The controller is adapted for coupling to a plurality of ultrasonic transducers. The controller include a multiplexer for selecting one of the plurality of ultrasonic transducers, signal processing means for processing an output of the selected ultrasonic transducer and controller means for providing parameters to the signal processing means based upon the selected ultrasonic transducer. The controller couples to a two wire 4–20 mA communication loop. The controller periodically excites the ultrasonic transducer to obtain a measurement. The controller stores power received from the two wire communication loop and excites the transducer using stored power. The controller is capable of providing power which exceeds that available directly from the two wire communication loop for a brief period of time. The controller provides a wet self-test whereby output level of the ultrasonic transducer is monitored while strength of the excitation signal provided to the ultrasonic transducer is decreased. The amount of decrease required for the output signal to pass a threshold level is an indication of the usefulness of the sensor.

26 Claims, 7 Drawing Sheets

CONTROLLER FOR ULTRASONIC SENSORS

BACKGROUND OF THE INVENTION

The present invention relates to ultrasonic sensors for measuring physical properties of materials. More particularly, the present invention relates to a controller for an ultrasonic sensor used in a 4–20 mA communication loop.

Various ultrasonic distance and level measuring and level measuring systems are known. For example, Ellinger et al. U.S. Pat. No. 4,815,323 teaches an "echo ranging" ultrasonic transducer transmitting an ultrasonic signal which is reflected from a liquid surface in an aircraft fuel container and then sensed. The round-trip time from sensing to receiving is measured and the fuel quantity and density are computed in a central processing unit as a function of the round trip time and stored data.

In another type of ultrasonic sensor as taught by U.S. Pat. No. 4,299,114 to Silvermetz et al., an ultrasonic transmission between transmit and receive transducers closes a feedback loop of a circuit which oscillates when feedback increases to a predetermined amount. When a material level in a container rises to a level where the transmit and receive transducers are mounted, the increased feedback through the material causes the circuit to oscillate. This type of sensor requires a relatively large difference between the amount of feedback when sensing a liquid and the amount of feedback when sensing a gas for stable operation. Undesired feedback through a sensor body can reduce stability, as well. If air is entrapped in the material, feedback can be reduced and sensing fails. In this type of sensor, misalignment of the transducers can reduce feedback through the materials so that sensing fails.

Ultrasonic transducers require a controller to control their operation. The controller operates the transducer elements, performs sensor test functions and provides a sensor output signal. There is a continual need for improvements in controllers used with ultrasonic sensors.

SUMMARY OF THE INVENTION

The present invention is an ultrasonic transducer for measuring a property of a material within a defined space (gap) as a function of a velocity at which ultrasonic signals travel through the defined space. A controller controls the ultrasonic transducer.

The controller preferably includes a multiplexer which is connected to a plurality of ultrasonic transducing elements. A signal processing stage follows the multiplexer. The controller selects one of the plurality of transducing elements through the multiplexer. The controller provides signal processing parameters to a signal processing stage which are related to the selected transducing element.

The ultrasonic transducer preferably is coupled to a two wire 4–20 mA communication loop. Power is received over the communication loop. The transducing element is periodically excited to obtain a measurement. Power received from the current loop is stored. The stored power is used to excite the transducing element. This circuitry briefly provides higher power output than is possible if power is drawn directly from the communication loop.

The controller preferably includes self-test circuitry for testing the integrity of the ultrasonic transducer. The controller excites the transducing element while monitoring the output of the transducing element. The relative strength of the excitation signal is decreased until the output falls below a threshold level. The strength of the excitation signal at which the output falls below the threshold is an indication of integrity and usefulness of the transducing element.

DETAILED DESCRIPTION OF THE PREFERRED EMBODIMENTS

Figure 1:
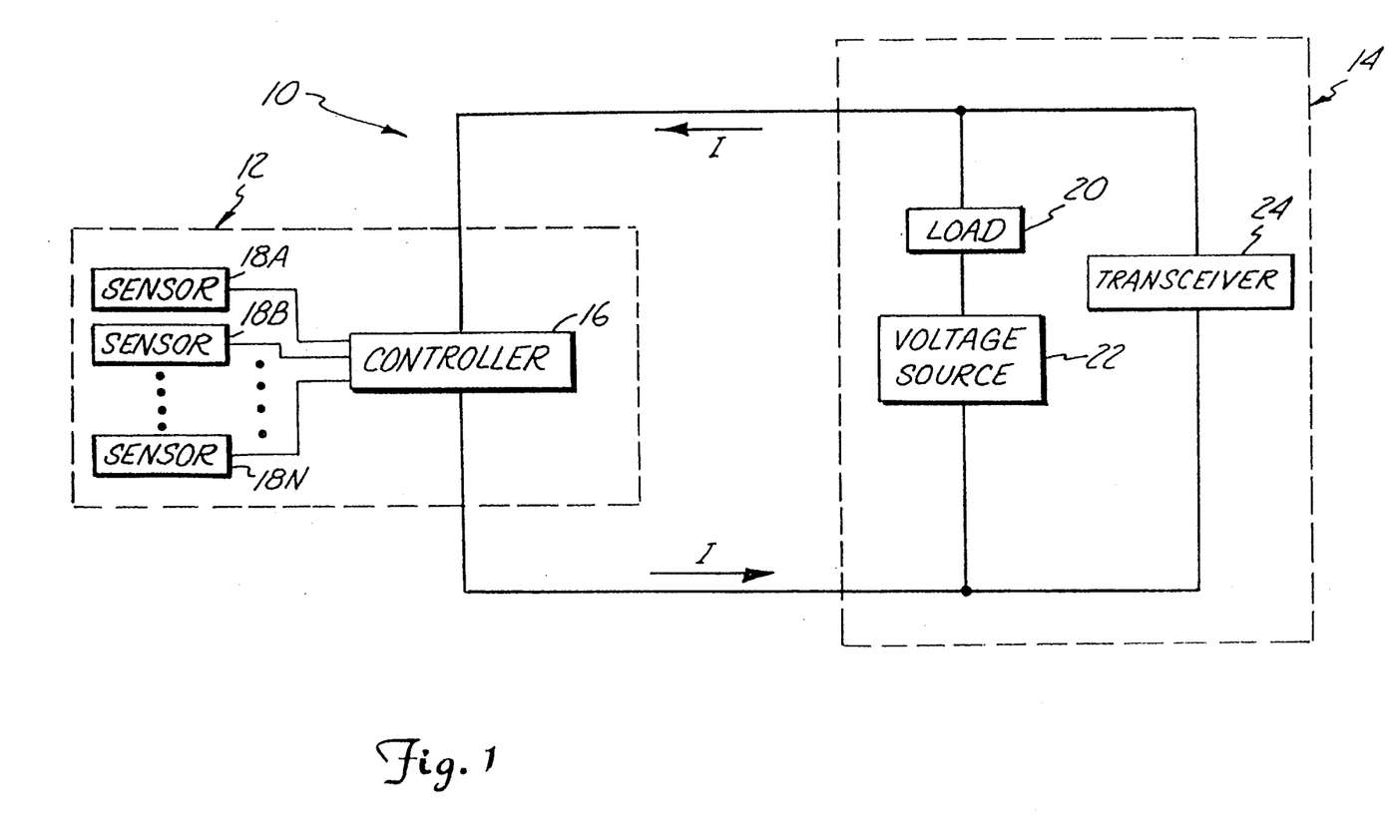
FIG. 1 shows a diagram of a two wire 4–20 mA current loop including an ultrasonic transducer circuitry in accordance with the present invention.

FIG. 1 is a diagram of a 4–20 mA communication loop 10. Communication loop 10 includes ultrasonic transducer circuitry 12 and control station circuitry 14. Ultrasonic transducer circuitry 12 includes controller 16 coupled to ultrasonic sensors 18A, 18B through 18N. Controller circuitry 14 includes load 20, voltage source 22 and transceiver 24.

In operation, communication loop 10 is used to carry signals between control station circuitry 14 and ultrasonic transducer circuitry 12. Ultrasonic transducer circuitry 12 transmits the signals by controlling current through communication loop 10. For example, a 4 mA signal represents a "zero" measurement while a 20 mA current signal represents a full scale measurement. Communication loop 10 can also carry information in other forms, for example a digital signal can be superimposed on the current level. The digital signal can be used to transmit commands from control station circuitry 14 to ultrasonic transducer circuitry 14. Control station circuitry 14 includes a voltage source 22 which provides power for communication loop 10. Transceiver 24 of control station circuitry 14 is used to send and receive information on communication loop 10. Transceiver 24 includes an interface output for communication with an operator, for example.

Controller 16 of ultrasonic transducer circuitry 12 selects one of the ultrasonic sensors 18A, 18B through 18N for measurement. Information obtained from one of the ultrasonic sensors 18A, 18B through 18N is converted into a usable form by controller 16 and transmitted over communication loop 10 for receipt by transceiver 24. Controller 16 selects which sensor 18A, 18B or 18N to monitor based upon commands received from transceiver 24. Communication loop 10 is typically implemented in industrial manufacturing or processing plants, for example. Ultrasonic transducer circuitry 12 is placed in a remote location and control station circuitry 14 is placed at a system control station.

Figure 2:
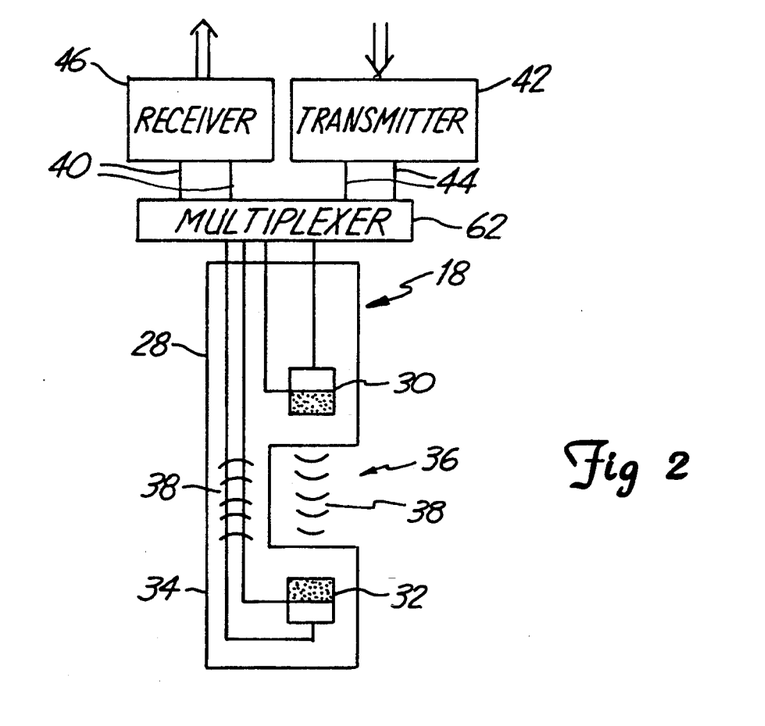
FIG. 2 is a sectional view of an ultrasonic sensor in accordance with the present invention.

FIG. 2 is a sectional view of an ultrasonic sensor 18, similar to sensors 18A, 18B through 18N. Sensor 18 includes a support structure 28, ultrasonic transmit transducer (crystal) 30 and ultrasonic receive transducer (crystal) 32. Support structure 28 includes stem 34 and gap 36. Stem 34 is also known as a bridge. A transducing element is formed by transducers 30 and 32 which are mounted to support structure 28 such that they transmit and receive ultrasonic signals 38 across gap 36 and along stem 34. Support structure 28 can be constructed out of a variety of materials such as metal or plastic. In one typical construction, transducers 30 and 32 are mounted in a pair of cavities in half-bodies of structure 28 which are secured to stem 34. Stem 34 is formed from a solid metal or plastic having a channel in which to route lead wires 40. The entire sensor 18 is then hermetically sealed.

Transmit transducer 30 is connected to transmitter 42 through electrical leads 44 and multiplexer 62. Transmitter 42 periodically supplies electronic transmit pulses on leads 44 to transducer 30. When transmitter 42 delivers a transmit pulse to transmit transducer 30, the pulse energizes (or excites) transducer 30 causing the transducer to resonate at its natural frequency. Transducer 30 emanates ultrasonic signals 38 which travel through gap 36 and stem 34. The ultrasonic signals that travel through gap 36 are referred to as a main waveform, while the signals that travel through stem 34 are referred to as a stem or self-test waveform.

Receive transducer 32 is connected to receiver 46 through electrical leads 40 and multiplexer 62. Receive transducer 32 converts ultrasonic signals 38 into electrical signals which are applied to leads 40. Sensor 18 is coupled to receiver 46 and transmitter 42 through multiplexer 62.

The attenuation of ultrasonic signals 38 crossing gap 36 is related to the density of the material in the gap and its acoustical transmission variation. Therefore, when gap 36 is void of liquid the attenuation of the main waveform is significantly greater than when liquid is present in the gap. The attenuation is particularly great at high frequencies, such as above several megahertz. When gap 36 is empty, the signal which travelled through the gap is substantially a null signal. When gap 36 is filled with a liquid, the main waveform is received by transducer 32. The main waveform causes transducer 32 to resonate and generate electrical signals on leads 40. As a result, the presence or absence of the main waveform at receive transducer 32 is representative of the presence or absence of a liquid within gap 36.

Sensor 18 can be used to measure physical properties of material within gap 36. For example, sensor 18 can measure liquid level in a vessel by sensing the presence or absence of liquid within gap 36. Sensor 18 can be secured to a flange mounted fitting, such as a standard NPT ¾ inch fitting. The fitting is then secured to a wall of a vessel containing material to be measured.

Figure 3:
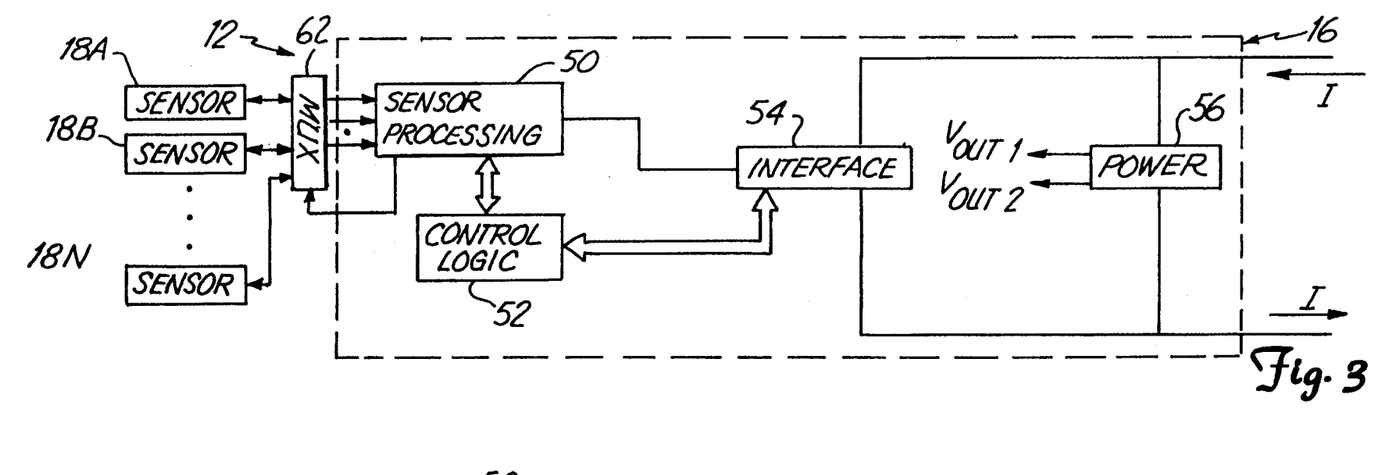
FIG. 3 is a block diagram of the ultrasonic transducer circuitry of FIG. 1.

FIG. 3 is a more detailed view of controller 16 shown in FIG. 1. Controller 16 includes sensor processing circuitry 50, control logic 52, interface 54, and power supply 56. Sensor processing circuitry 50 is coupled to sensors 18A, 18B through 18N. Sensor processing circuitry 50 is also connected to control logic 52 and interface 54. Interface 54 is coupled to the two wire current loop and is also connected to control logic 52. Controller 16 includes power supply 56 coupled to the two wire current loop. Power supply 56 provides two voltage outputs, $V_{out1}$ and $V_{out2}$. Outputs $V_{out1}$ and $V_{out2}$ are coupled to sensor processing circuitry 50, control logic 52, and interface 54 and provide power to those circuits.

Interface 54 is coupled to the two wire current loop and is used to send and receive information on the current loop. Control logic 52 controls operation of sensor processing circuit 50 and is in communication with control station circuitry 14 through interface 54 over the two wire current loop 10. Power supply 56 provides regulated power to sensor processing circuitry 50, control logic 52, and interface 54. Power supply 56 draws power from the two wire current loop.

Figure 4:
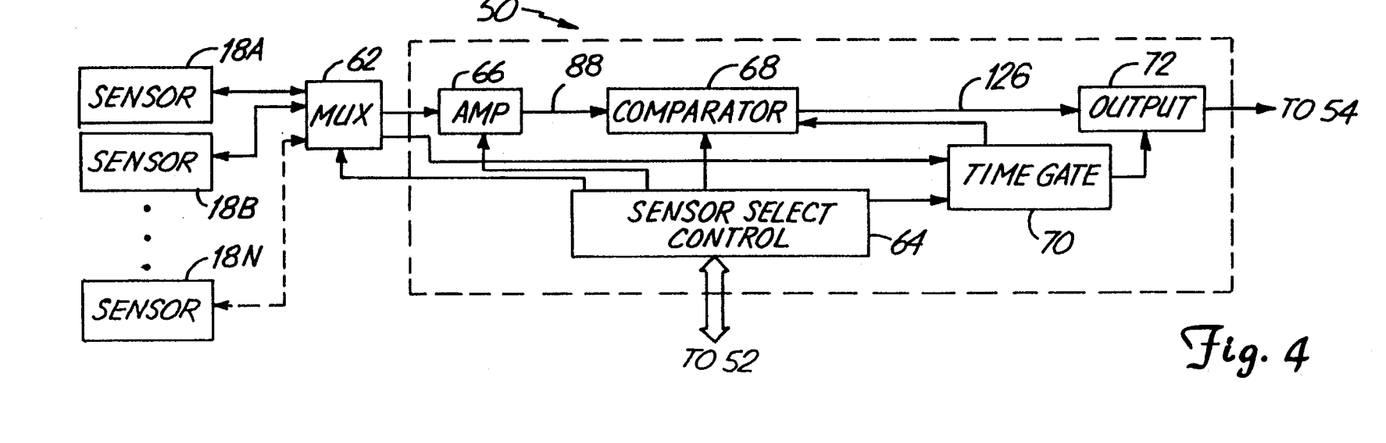
FIG. 4 is a block diagram of sensor processing circuitry.

FIG. 4 is a block diagram of sensor processing circuitry 50. Sensor processing circuitry 50 includes transmitter 42, receiver 46, multiplexer 62, and sensor select control 64. Multiplexer 62 is coupled to sensors 18A, 18B through 18N. Sensor processing circuitry 50 includes amplifier 66, comparator 68, time gate 70, and output stage 72. Amplifier 66 is connected to the output of multiplexer 62 through receiver 46 and provides an amplified input to comparator 68. Time gate 70 is connected to the output of comparator 68. Output stage integrator block 72 is connected to the output of time gate 70. The output of output stage 72 is connected to interface 54 shown in FIG. 3. Sensor select control 64 is connected to control logic 52. Sensor select control 64 provides control signals to multiplexer 62, amplifier 66, comparator 68, and time gate 70.

In oscillator-type ultrasonic sensors used in the prior art, the transmit and receive transducers are connected in a feedback loop which is stable when the gap is void of process material. This is called a "dry" condition. When material enters the gap the circuit oscillates. This is called a "wet" condition. A number of problems are inherent with the oscillator-type design that are not encountered with the present invention. First, the wet/dry signal ratio may not be large enough for stable operation. This can be caused by too much signal passing through the stem of the sensor body, or when the attenuation of air is only slightly greater than the attenuation of the process material. Second, the consistency of the process material can affect the sensor performance. If the material has a high concentration of entrapped air, the circuit may not oscillate.

In the present invention, when a liquid level is measured, the amplitude of the main signal is measured in a main time window, while the signal from the stem is separated in time (either before or after the main time window) depending on the time delay through the stem, so that is does not present interference. On the other hand, when a material density is measured, the parameter measured is time, not amplitude. Amplitude is not used to sustain oscillation as in the prior art.

Figure 5:
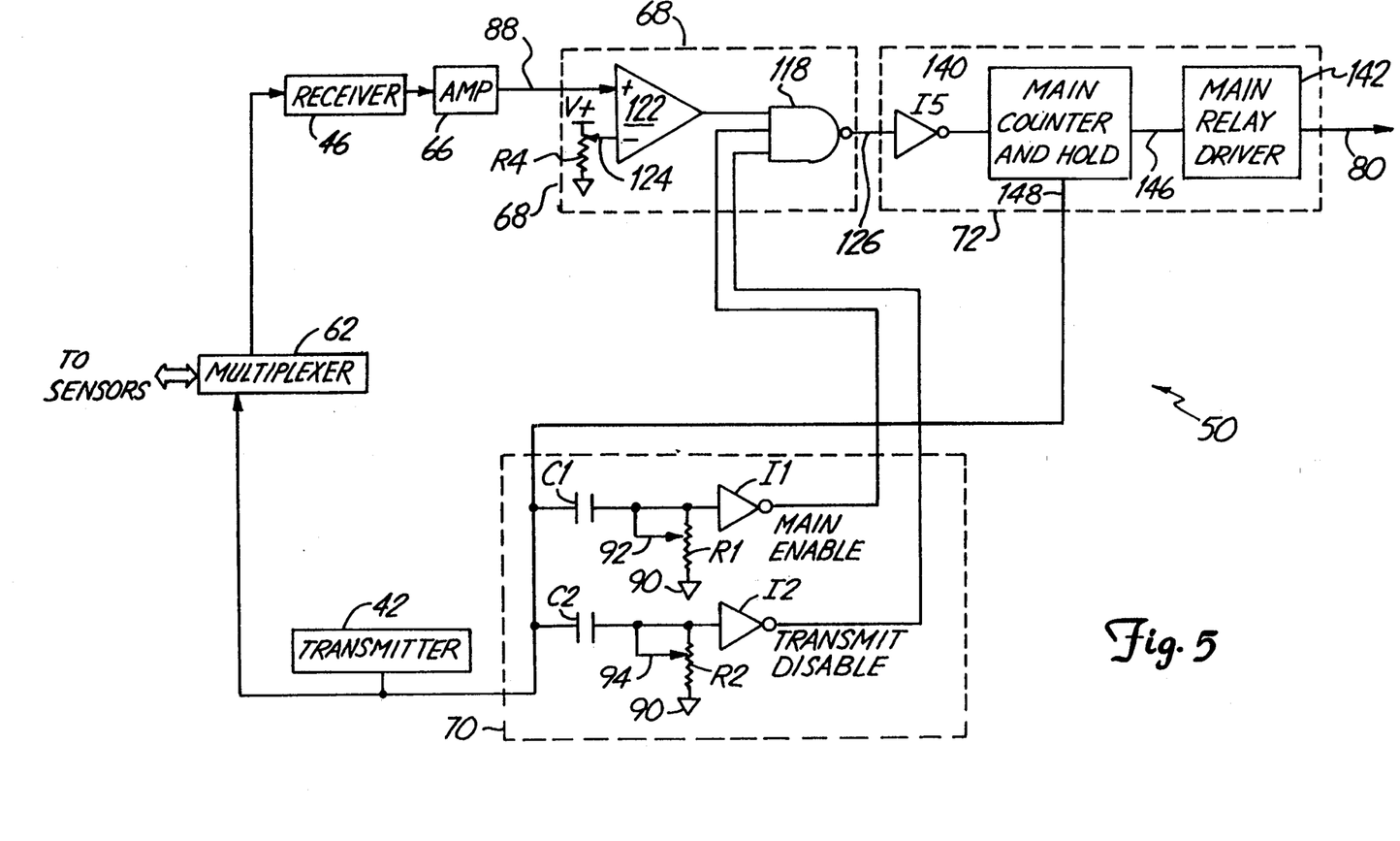
FIG. 5 is a schematic diagram of sensor processing circuitry.

FIG. 5 is a schematic diagram of sensor processing circuitry 50 in accordance with the present invention, for simplicity sensor select control 64 is not shown in FIG. 5. The circuit includes transmitter 42, receiver 46, time gate 70, main waveform detector/comparator 68, and main waveform integrator 72. Time gate 70 generates enable signals which "gate" detector/comparator 68 at certain times to open windows where integrator 72 looks for the main waveform received by receiver 46. Integrator 72 provides output 80 representative of the presence or absence of the main waveform within its corresponding time windows. The presence or absence of the main waveform is representative of the presence or absence of a liquid within gap 36 of sensor 18.

Main waveform detector/comparator 68 is connected between amplifier 66 and main waveform integrator 72. Comparator/detector 68 includes resistor R4, comparator 122 and NAND gate 118. Resistor R4 is connected between voltage supply terminal V+ and ground terminal 90. Resistor R4 is a variable resistor having a center tap 124 connected to an inverting input of comparator 122. A noninverting input of comparator 122 is connected to amplifier output 88. The output of comparator 122 is connected to NAND gate 118. NAND gate 118 generates a main waveform detector output 126.

Time gate 70 includes capacitors C1 and C2, variable resistors R1 and R2 having center taps 92 and 94, respectively, and inverters I1 and I2. Capacitor C1 is connected between the output of transmitter 42 and the input of inverter I1. Variable resistor R1 is also connected between the input of inverter I1 and electrical ground 90. Center tap 92 of variable resistor R1 is connected to input of inverter I1. Capacitor C2 is connected between the output of transmitter 42 and the input of inverter I2. Variable resistor R2 is connected between the input to inverter I2 and electrical ground 90. Center tap 94 of variable resistor R2 is connected to the input of inverter I2. The outputs of inverters I1 and I2 are connected to the inputs of NAND gate 118.

Intergrator 72 includes inverter I5, main counter and hold 140, and main relay driver 142. The input of inverter I5 is connected to the output of NAND gate 118. The output of inverter I5 is connected to main counter and hold 140. Main counter and hold is also connected to the output of transmitter 42. The output of main counter and hold 140 is connected to main relay driver 142.

Transmitter 42 is connected between transmit transducer 30 and time gate 70. Transmitter 42 includes an oscillator circuit which operates with repetition rates typically from 10 Hz to 5 KHz. With each cycle of the oscillator, transmitter 42 excites transmit transducer 30 with a voltage transmit pulse lasting between one-fourth and one-half of the transmit transducer's natural transmit period. The voltage level is selected based upon the sensor and the application. The transmit pulse causes transmit transducer 30 to resonate and generate ultrasonic signals which travel across gap 36 and stem 34 (shown in FIG. 2). The ultrasonic signals 38 are received by receive transducer 32. Receive transducer 32 includes a high pass filter which applies a filtered signal to amplifier 66.

Time gate windows (discussed below) are generated by time gate 70 in response to a rising edge of the transmit pulse generated by transmitter 42. Time gate 70 includes capacitors C1, and C2, resistors R1, and R2, and inverters I1, and I2. Capacitor C1 is connected between transmitter 42 and inverter I1. Resistor R1 is connected between ground terminal 90 and the node between capacitor C1 and inverter I1. Resistor R1 is a variable resistor having a center tap 92 which is connected to the node between capacitor C1 and inverter I1. Inverter I1 generates a main waveform enable signal at its output.

Capacitor C2 is connected between transmitter 42 and inverter I2. Resistor R2 is connected between ground terminal 90 and the node between capacitor C2 and inverter I2. Resistor R2 is a variable resistor having a center tap 94 which is connected to the node between capacitor C2 and inverter I2. Inverter I2 generates a transmit pulse disable signal at its output.

Figure 7:
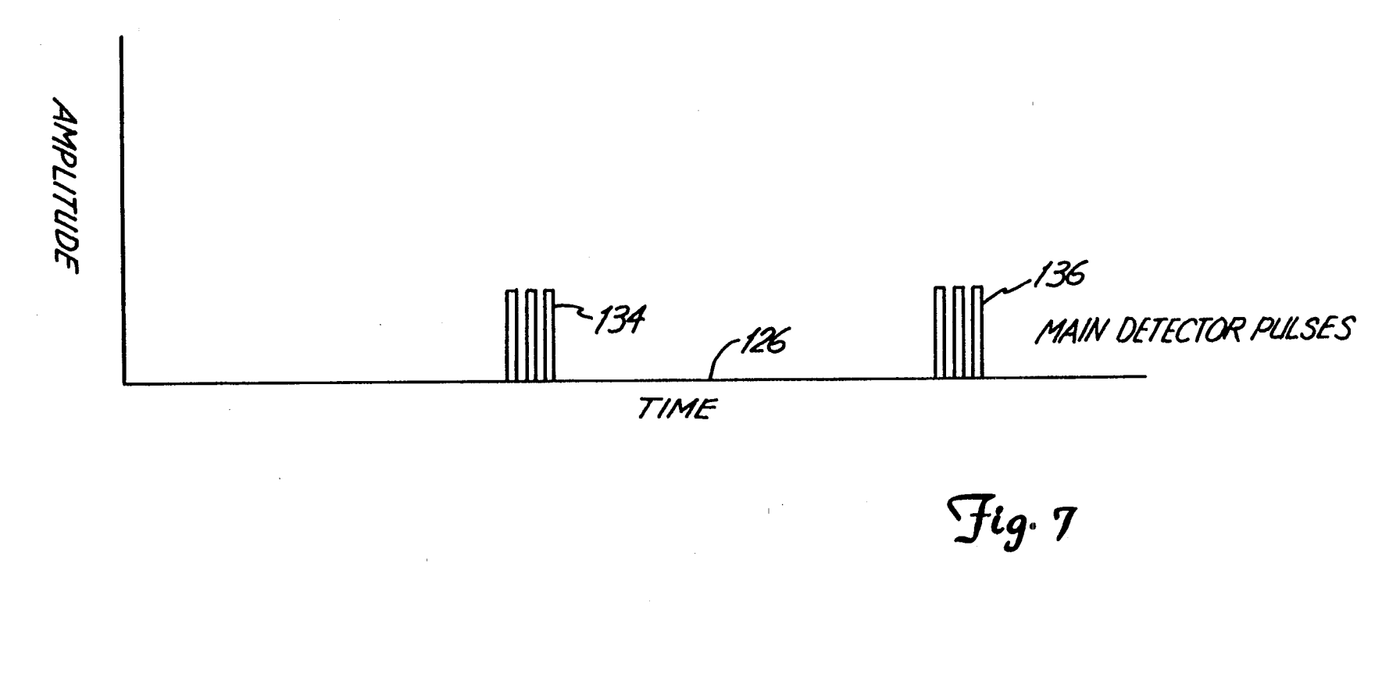
FIG. 7 is a graphical representation of a signal from the circuitry of FIG. 5.

The rising edge of each transmit pulse is integrated by two RC time constants within time gate generator 70. Capacitor C1 and resistor R1 form a first time constant which determines the length of time the main waveform enable signal is active (logic HIGH). Capacitor C2 and resistor R2 form a second time constant which determines the length of time the transmit pulse disable signal is active. These enable signals are illustrated in FIG. 7.

Figure 6:
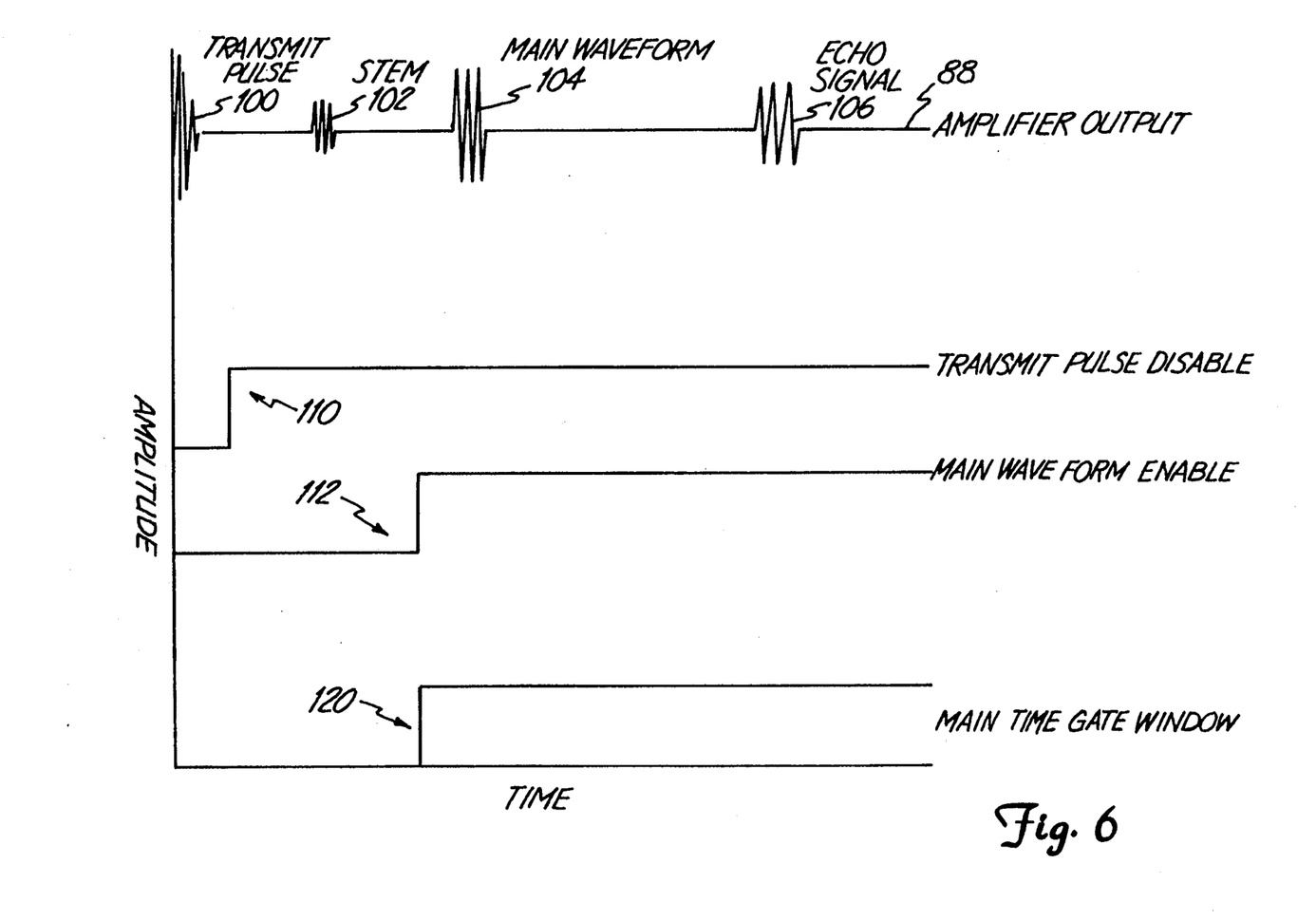
FIG. 6 is a timing diagram which provides a graphical representation of various signals from the circuitry shown in FIG. 5.

FIG. 6 is a timing diagram which provides a graphical representation of various signals within the time gate ultrasonic sensor circuit shown in FIG. 4 during one cycle of transmitter 42. The graph represents signal amplitude as a function of time. Amplifier output 88 is shown at the top of the diagram. The first waveform to arrive is transmit pulse waveform 100. This waveform 100 is generated by transmit transducer 30 when it begins to vibrate. The second waveform to arrive is stem or self-test waveform 102 which traveled through sensor stem 34. This is delayed because ultrasonic signals travel faster in solids than in liquids and in gases. The third waveform to arrive is main waveform 104 which traveled through a liquid in sensor gap 36. The fourth waveform to arrive is an echo signal 110 of main waveform 104 caused by reflections in gap 36.

Waveform 110 illustrates the transmit pulse disable signal. The transmit pulse disable signal goes LOW at the rising edge of the transmit pulse and remains LOW for the second time constant determined capacitor C2 and resistor R2. After the second time constant, the transmit pulse disable signal goes HIGH. The second time constant is selected to temporarily disable detector/comparator 68 to prevent detection of transmit pulse waveform 100.

Waveform 112 illustrates the main waveform enable signal. At the rising edge of the transmit pulse, main waveform enable signal 112 goes LOW, and remains LOW for the first time constant determined by capacitor C1 and resistor R1. After the first time constant, main waveform enable signal 112 goes HIGH. Main waveform enable signal 112 and transmit pulse disable signal 110 are logically NANDed together at NAND gate 118 (FIG. 5) to generate main waveform time gate window 120 (shown in FIG. 6). Main waveform time gate window 120 enables main waveform detector/comparator block 68 to detect the presence or absence of main waveform 104 only during the main waveform time gate window. If main waveform 104 is present within main waveform time gate window 120, the ultrasonic signals traveled through a liquid. If main waveform 104 is not present within main waveform time gate window 120, the ultrasonic signals traveled through a gas, because it takes much longer to receive the main waveform signal. Further, main waveform 104 attenuates in air to such an extent that the signal received at receive transducer 16 is substantially a null signal. The main waveform time gate window 120 closes at the end of each cycle of transmitter 30. However, time gate generator block 70 can easily be modified to close the main waveform time gate window prior to the end of each cycle.

Center tap 124 provides a main waveform threshold voltage at the inverting input of comparator 122. Comparator 122 compares amplitude of amplifier output 88 to the main waveform threshold voltage. The main waveform threshold voltage is set by adjusting center tab 124 of resistor R4. The threshold is adjusted to represent an expected amplitude of main waveform 104 (shown in FIG. 6) which arrives during main waveform time gate window 120. This value will vary depending upon the type of transducers used, the excitation frequency, the dimensions of the sensor, the physical properties of the material within the gap and the gain of amplifier 66. The output of comparator 122 is connected to NAND gate 118 together with main waveform enable signal 112 and transmit pulse disable signal 110 such that main waveform 104 is detected only during main waveform time gate window 120.

Main waveform detector output 126 is illustrated in FIG. 7. FIG. 7 is a graphical representation of the amplitude of detector waveforms 126 as a function of time. The main waveform detector output 126 includes a series of pulses 134 which correspond to main waveform 104 (shown in FIG. 6) and includes a series of pulses 136 which correspond to echo waveform 106. The presence of pulses 134 in main waveform detector output 132 indicates that main waveform 104 was present within main waveform time gate window 120.

The main waveform detector output 126 is integrated by integrator 72. Integrator 72 includes inverter I5, main waveform counter and hold circuit 140 and main waveform relay driver 142. Inverter I5 is connected between NAND gate 118 and main waveform counter and hold circuit 140. Main waveform counter and hold circuit 140 is connected between inverter I5 and main waveform relay driver 142. Main waveform counter and hold circuit 140 counts the number of pulses received from NAND gate 118 during each cycle of the oscillator in transmitter 30. When the number of counted pulses exceeds a given number (such as 3) during one cycle of the oscillation, the counter generates a signal at output 146 which indicates main waveform 104 was present during main waveform time gate window 120.

Signal 146 is applied to main waveform relay driver 142 which generates main waveform output signal 80. Main waveform counter and hold circuit 140 includes a reset input 148 which is connected to transmitter 30. At the beginning of each transmit cycle of transmitter 30, transmitter 30 supplies a reset pulse which resets main counter and hold circuit 140. By counting the number of pulses during a given cycle, circuit 140 helps to eliminate false detection of main waveform 104.

As mentioned, the second set of pulses 136 shown in FIG. 7 represents echo waveforms 106 (shown in FIG. 6) within sensor gap 36. The main waveform threshold voltage can be adjusted so that echo waveforms 106 in amplifier output 88 will not generate pulses on output 126 for main waveform counter and hold circuit 140. However, this is not necessary because the counter will hold its state after detecting the given number of pulses until it has been reset.

Main waveform output signal 80 is representative of the presence or absence of a liquid within gap 36 of sensor 18. The time gate ultrasonic sensor of the present invention can be used to determine when a liquid in a tank rises to a specified level. Sensor 18 is positioned at the specified level. When the liquid rises and enters gap 36, the velocity at which the ultrasonic signals travel through the gap increases such that the main waveform arrives at receive transducer I6 within main waveform time gate window 120. Main waveform output signal 80 will indicate that the liquid is present within gap 36.

The time gate configuration can measure density and level simultaneously because the time it takes the ultrasonic signals to travel through a material is related to the density of the material. The density measurement is made by creating additional time gate windows that are adjusted to reflect material density based on signal velocity through the material. The sensor can detect an interface between two materials in the gap based on change of signal velocity if the density of the two materials is known.

In operation, sensor select control 64 shown in FIG. 4 controls multiplexer 62, the gain of amplifier 66, and the resistance of variable resistors R1, R2, and R4. Sensor select control 64 receives information from control logic 52 indicating which sensor, 18A, 18B or 18N is selected by control station circuitry 14. This information is used by sensor select control 64 to switch multiplexer 62 to the selected sensor 18A, 18B or 18N. Each sensor, 18A, and 18B through 18N may have different characterizing parameters and uses. These characterizing parameters are used to determine the appropriate operating parameters: amplifier gain, comparator threshold level and time gate position and duration. The selected parameters are stored in sensor select control 64. Sensor select control 64 adjusts the gain of amplifier 66, the resistance of variable resistor R4 (the comparator threshold level) and the resistance of variable resistors R1 and R2 (time gate position and duration) to match the selected sensor. This reduces the number of circuit component required in multisensor installations.

The invention as shown in FIG. 4 allows one controller to be compatible with various types of sensors required for different applications. For example, ½ inch gap-type sensors are used for standard liquids while slot-type sensors are required for highly aerated liquids with different acoustical properties. Furthermore, for some viscous liquids gap-type sensors with large gap sizes (more than 2 inches) are needed.

Every sensor type can be characterized by the following parameters:
Wet signal level;
Dry signal level;
Propagation time of the ultrasonic pulse through the liquid between the transmitting crystal and the receiving crystal;
Propagation time of the ultrasonic pulse through the sensor body from the transmitting crystal to the receiving crystal.

These four sensor parameters affect three parameters of the signal processing circuitry: amplifier gain, comparator threshold level, and time gate position and duration. With the present invention, these three parameters of sensor processing circuitry 50 are under the control of sensor select control 64. The parameters can be preprogrammed in sensor select control 64 or the system can be supplied with switches which enable an operator to select the parameters based upon various types of sensors and their application. The time gate circuitry is well suited for multiplexer implementation because prior art systems used feedback loops which are difficult to multiplex.

Figure 8:
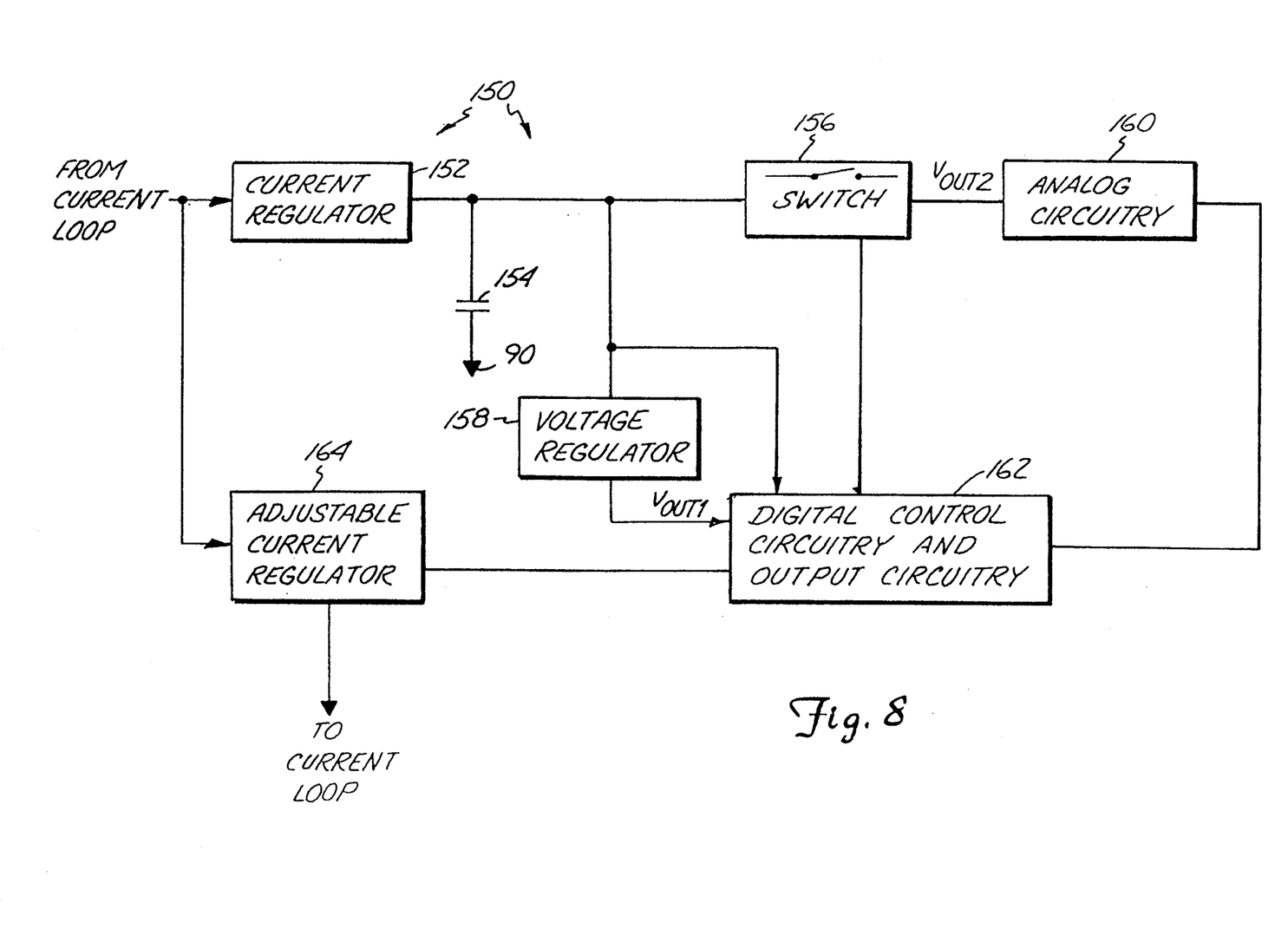
FIG. 8 is a diagram of power supply circuitry.

FIG. 8 is a block diagram that shows the relationship between power supply 56 and sensor processing circuitry 50, control logic 52, and interface 54 of FIG. 3. Block diagram 150 of FIG. 8 includes current regulator 152, capacitor 154, switch 156, voltage regulator 158, analog circuitry 160, digital control circuitry and output circuitry 162, and adjustable current regulator 164. For simplicity, the analog components of sensor processing circuitry 50 are shown generally at analog circuitry 160. Similarly, control logic 52, interface 54, and the digital components of sensor processing circuitry 50 are shown generally as digital control circuitry and output circuitry 162 in FIG. 8.

Current regulator 152 is connected to the two wire communication loop. The output of current regulator 152 is connected to capacitor 154, voltage regulator 158, switch 156, and digital control circuitry and output circuitry 162. The other terminal of capacitor 154 is connected to ground 90. Switch 156 has a control input connected to digital control circuitry and output circuitry 162 and an output $V_{out2}$ connected to analog circuitry 160. The output of analog circuitry 160 is provided to digital control circuitry and output circuitry 162. The output $V_{out1}$ of voltage regulator 158 is connected to digital control circuitry and output circuitry 162. Adjustable current regulator 164 has an input connected to the communication loop, an output connected to electrical ground 90, and a control input connected to digital control circuitry and output circuitry 162.

In a typical installation, an ultrasonic liquid level sensor uses approximately 50 mA of current for operation. About 95% of this current is used by the analog circuitry. However, in a two wire 4–20 mA communication loop, the maximum current drawn by the circuitry cannot be greater than 4 mA. In accordance with the present invention, the circuitry shown in FIG. 8 operates an ultrasonic sensor on power drawn only from the two wire current loop and does not draw more then 4 mA of current. The circuitry of FIG. 8 is capable of providing 50 mA to analog circuitry 160 for a brief period of time. For example, in one embodiment of the present invention, analog circuitry 160 is powered periodically for a duration of 1 millisecond. The system uses 900 microseconds for stabilization and 100 microseconds for ultrasonic sensor measurement.

In FIG. 8, current regulator 152 receives current from the two wire communication loop shown in FIG. 1. Current regulator 152 charges capacitor 154. Voltage regulator 158 provides a regulated voltage $V_{out1}$ to digital control circuitry and output circuitry 162. Digital control circuitry and output circuitry 162 also monitors the voltage on capacitor 154. When capacitor 154 charges to 10 volts, digital control circuitry and output circuitry 162 closes switch 156 for 1 millisecond. This provides a voltage output on $V_{out2}$ to analog circuitry 160. Capacitor 154 should have a large enough value to provide the required current to analog circuitry 160 for the necessary duration. For example, in one embodiment capacitor 154 has a sufficiently large capacitance to provide a current of 50 mA for a 1 millisecond duration without dropping below 9 volts. After analog circuitry 160 has obtained a reading from ultrasonic sensor 18 (after 1 millisecond) digital control circuitry and output circuitry 162 turns switch 156 off allowing capacitor 154 to recharge to 10 volts. In one embodiment, this recharging takes approximately 19 milliseconds. When capacitor 154 is fully recharged to 10 volts, the cycle is repeated. Digital control circuitry and output circuitry 162 adjusts the current through the two wire current loop by controlling adjustable current regulator 164.

The circuitry of FIG. 8 permits analog circuitry to draw more than 4 mA (a "zero" on the current loop) for short period of time. This is particularly well suited for ultrasonic sensors using the time gate circuitry described above because the sensors are pulsed for a period of time within a window.

Control logic 52 shown in FIG. 3 is capable of performing a self-test function. Typical prior art self-test methods required the test to be performed "dry," without the presence of any liquid. The present invention provides a "wet" self-test in which the workability and reliability of sensor 18 is determine in a particular environment. That is, the wet self test is an indication of the usefulness and accuracy of the sensor. In a wet self-test, sensor 18 is emersed in the fluid it is measuring. The prior art dry self-test method have a number of fallbacks. For example, if the liquid is aerated of attenuative due to its acoustical properties, or if the sensor is coated and decoding thickness increases with time the prior art self-test modes might falsely indicate a good sensor.

Figure 9:
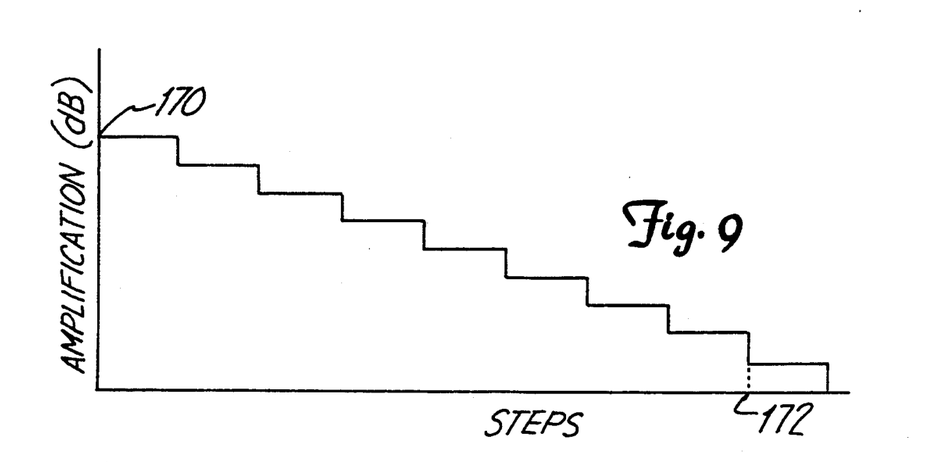
FIG. 9 is a graph of amplification in dB versus number of steps and is used to illustrate a wet self-test in accordance with the present invention.

The wet self-test of the present invention can be implemented completely automatically in a microprocessor contained in control logic 52. In this embodiment, a sensor 18A, 18B or 18N, is select through multiplexer 62. Sensor select control 64 controls the amplification of amplifier 66 as shown in FIG. 9. The amplification is set to initial value 17 and a sensor measurement is obtained. The amplification is then decreased by one dB and another measurement is taken. This process can continue until output 88 drops below a predetermined minimum threshold level. In a preferred embodiment, this threshold level corresponds to the minimum signal level which correspondence to a "wet" sensor output signal. This point is shown as 172 in FIG. 9.

The number of steps required to reach point 172 is counted. The number of steps can be compared to measurements taken when the sensor was new. Additionally, the number can be checked to see if it falls within a specified range. This information is stored in memory contained in control logic 52. Over time, it can be expected that the number of steps will decrease as the sensor degrades. The decrease can be monitored and the sensor can be replaced before it fails. Following completion of the test, amplifier gain is returned to normal.

The time gate ultrasonic sensor of the present invention can be used in virtually any application to measure physical properties of material within a defined space. Although the present invention has been described with reference to preferred embodiments, workers skilled in the art will recognize that changes may be made in form and detail without departing from the spirit and scope of the invention. For example, the comparisons between amplifier output 88 (shown in FIG. 5) and the threshold voltage can be done with a microprocessor that establishes the time gate windows. A software program for computer control can also be used to provide the same comparisons. DSP (Digital Signal Processing) integrated circuits can also be used to replace the circuitry shown.

Although the present invention has been described with reference to preferred embodiments, workers skilled in the art will recognize that changes may be made in form and detail without departing from the spirit and scope of the invention.

What is claimed is:

1. An apparatus for controlling operation of ultrasonic transducers, comprising:
    a multiplexer adapted for coupling to a plurality of ultrasonic transducers and having a multiplexer output and a selection input for selecting which of the plurality of ultrasonic transducers is coupled to the multiplexer output;

signal processing means for processing the multiplexer output based upon signal processing parameters received from a parameter input and providing a processed output; and controller means for receiving an input related to a selected transducer, providing a signal to the selection input of the multiplexer whereby the selected transducer is coupled to the multiplexer output, and providing signal processing parameters related to the selected transducer to the signal processing means, the controller means including an interface for coupling to a communication loop and wherein the controller input related to a selected transducer is received over the communication loop.

2. The apparatus of claim 1 wherein the signal processing means includes an amplifier and one of the signal processing parameters provided by the controller means relates to amplifier gain.

3. The apparatus of claim 1 wherein the signal processing means includes a comparator and one of the signal processing parameters provided by the controller means is related to comparator threshold level.

4. The apparatus of claim 1 wherein the signal processing means includes time gates circuitry and one of the signal processing parameters provided by the controller means relates to a time gate window.

5. The apparatus of claim 1, and further comprising:
means for periodically exciting the selected ultrasonic transducer through the multiplexer; and
means, coupled to the interface, for storing power received from the two wire communication loop and providing stored power to the means for periodically exciting.

6. The apparatus of claim 1 and further comprising:
means for exciting a selected ultrasonic transducer through the multiplexer and obtaining a transducer output signal;
wherein the controller means includes:
means for decreasing strength of an excitation signal provided to the ultrasonic transducer; and
comparator means for comparing the strength of the transducer output signal with a reference signal level and producing an output based upon the comparison which is representative of a wet self-test.

7. An ultrasonic transducer for coupling to a two wire 4–20 mA communication loop, comprising:
interface means for receiving power from the two wire communication loop and transmitting information related to transducer measurements over the two wire communication loop;
an ultrasonic transducing element;
means for periodically exciting the ultrasonic transducing element, obtaining a transducer measurement and providing the interface means with information related to a transducer measurement; and
means, coupled to the interface means, for storing power received from the two wire communication loop and providing stored power to the means for periodically exciting.

8. The ultrasonic transducer of claim 7 wherein the means for storing power comprises a capacitor.

9. The ultrasonic transducer of claim 7 wherein the interface means comprises:
a current regulator for receiving current from the two wire communication loop and providing a regulated current output to the means for storing power; and an adjustable current regulator for regulating current through the two wire current loop whereby the current through the two wire communication loop is related to a sensor measurement.

10. The ultrasonic transducer of claim 7 wherein the means for periodically exciting the ultrasonic transducing element includes a switch coupled between the means for storing power and the ultrasonic transducing element.

11. An ultrasonic transducer for measuring a property of a material, comprising:
an ultrasonic transducing element;
means for exciting the ultrasonic transducing element;
means for receiving a transducer output signal from the ultrasonic transducing element;
means for decreasing strength of an excitation signal provided to the ultrasonic transducing element by the means for exciting; and
comparator means for comparing strength of the transducer output signal with a threshold level and producing an output based upon the comparison which is related to a wet self-test.

12. The ultrasonic transducer of claim 11 wherein the means for decreasing strength operates in incremental steps.

13. The ultrasonic transducer of claim 12 including means for counting a number of steps required to decrease strength of the excitation signal before the transducer output signal achieves the threshold level.

14. The ultrasonic transducer of claim 13 including means for storing a specified number of steps related to a sensor specification.

15. An apparatus for controlling operation of ultrasonic transducers, comprising:
a multiplexer adapted for coupling to a plurality of ultrasonic transducers and having a multiplexer output and a selection input for selecting which of the plurality of ultrasonic transducers is coupled to the multiplexer output;
signal processing means for processing the multiplexer output based upon signal processing parameters received from a parameter input and providing a processed output;
controller means for receiving an input related to a selected transducer, providing a signal to the selection input of the multiplexer whereby the selected transducer is coupled to the multiplexer output, and providing signal processing parameters related to the selected transducer to the signal processing means;
interface means for receiving power from a two wire communication loop and transmitting the processed output over the two wire communication loop;
means for periodically exciting the selected ultrasonic transducer; and
means, coupled to the interface means, for storing power received from the two wire communication loop and providing stored power to the means for periodically exciting.

16. The apparatus of claim 15 wherein the signal processing means includes an amplifier and one of the signal processing parameters provided by the controller means relates to amplifier gain.

17. The apparatus of claim 15 wherein the signal processing means includes a comparator and one of the signal processing parameters provided by the controller means is related to a comparator threshold level.

18. The apparatus of claim 15 wherein the signal processing means includes time gates circuitry and one of the signal processing parameters provided by the controller means relates to a time gate window.

19. The apparatus of claim 15 wherein the controller input related to a selected transducer is received over the two wire communication loop.

20. The apparatus of claim 15 and further comprising:
wherein the controller means includes:
means for decreasing strength of an excitation signal provided to the ultrasonic transducer; and
comparator means for comparing the strength of the transducer output signal with a reference signal level and producing an output based upon the comparison which is representative of a wet self-test.

21. An apparatus for controlling operation of ultrasonic transducers, comprising:
a multiplexer adapted for coupling to a plurality of ultrasonic transducers and having a multiplexer output and a selection input for selecting which of the plurality of ultrasonic transducers is coupled to the multiplexer output;
signal processing means for processing the multiplexer output based upon signal processing parameters received from a parameter input and providing a processed output;
controller means for receiving an input related to a selected transducer, providing a signal to the selection input of the multiplexer whereby the selected transducer is coupled to the multiplexer output, and providing signal processing parameters related to the selected transducer to the signal processing means;
means for exciting a selected ultrasonic transducing element and obtaining a transducer output signal;
wherein the controller means includes:
means for decreasing strength of an excitation signal provided to the ultrasonic transducing element; and
comparator means for comparing the strength of the transducer output signal with a reference signal level and producing an output based upon the comparison which is representative of a wet self-test.

22. The apparatus of claim 21 wherein the signal processing means includes an amplifier and one of the signal processing parameters provided by the controller means relates to am amplifier gain.

23. The apparatus of claim 21 wherein the signal processing means includes a comparator and one of the signal processing parameters provided by the controller means is related to comparator threshold level.

24. The apparatus of claim 21 wherein the signal processing means includes time gates circuitry and one of the signal processing parameters provided by the controller means relates to a time gate window.

25. The apparatus of claim 21 wherein the controller means includes an interface for coupling to a two wire communication loop and wherein the input related to a selected transducer is received over the two wire communication loop.

26. The apparatus of claim 21, and further comprising:
interface means for receiving power from a two wire communication loop and transmitting the processed output over the two wire communication loop;
means, coupled to the interface means, for storing power received from the two wire communication loop and providing stored power to the means for exciting.

* * * * *

UNITED STATES PATENT AND TRADEMARK OFFICE
CERTIFICATE OF CORRECTION

PATENT NO. : 5,437,178
DATED : August 1, 1995
INVENTOR(S) : Alex Esin, Lawrence J. Jones, Boris Rosselson and Martin N. Sorenson It is certified that error appears in the above-indentified patent and that said Letters Patent is hereby corrected as shown below:

Claim 26, Col. 14, line 34, insert --and-- after ";".

Signed and Sealed this

Fifth Day of March, 1996

Attest:

BRUCE LEHMAN

*Attesting Officer*       *Commissioner of Patents and Trademarks*